(12) United States Patent
Ouchi

(10) Patent No.: US 6,390,973 B1
(45) Date of Patent: May 21, 2002

(54) ENDOSCOPE FOR ULTRASONIC EXAMINATION AND SURGICAL TREATMENT ASSOCIATED THERETO

(75) Inventor: Teruo Ouchi, Saitama (JP)

(73) Assignee: Asahi Kogaku Kogyo Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/337,266

(22) Filed: Jun. 22, 1999

(30) Foreign Application Priority Data

Jun. 25, 1998 (JP) ............................................ 10-178505
Jun. 25, 1998 (JP) ............................................ 10-178506

(51) Int. Cl.[7] ................................................. A61B 8/12
(52) U.S. Cl. ........................ 600/113; 600/104; 600/153; 600/463
(58) Field of Search ................................ 608/104, 106, 608/107, 170, 153, 113, 462–467

(56) References Cited

U.S. PATENT DOCUMENTS

| | | | | |
|---|---|---|---|---|
| 4,224,929 A | * | 9/1980 | Furihata | 600/107 |
| 4,279,247 A | * | 7/1981 | Kinoshita | 600/170 |
| 4,407,273 A | * | 10/1983 | Ouchi | 600/107 |
| 4,436,087 A | * | 3/1984 | Ouchi | 600/106 |
| 4,582,067 A | * | 4/1986 | Silverstein et al. | 600/462 |
| 5,456,258 A | | 10/1995 | Kondo et al. | |
| 5,499,630 A | | 3/1996 | Hiki et al. | |
| 5,596,991 A | * | 1/1997 | Tanaka | 600/462 |

FOREIGN PATENT DOCUMENTS

| | | |
|---|---|---|
| JP | 62-58255 | 12/1987 |
| JP | 6-30937 | 2/1994 |
| JP | 6-105847 | 4/1994 |
| JP | 6-55605 | 8/1994 |
| JP | 7-4374 | 1/1995 |
| JP | 7-143985 | 6/1995 |
| JP | 7-171150 | 7/1995 |
| JP | 8-131442 | 5/1996 |
| JP | 8-140976 | 6/1996 |

* cited by examiner

*Primary Examiner*—John Mulcahy
(74) *Attorney, Agent, or Firm*—Greenblum & Bernstein, P.L.C.

(57) ABSTRACT

In an endoscope for ultrasonic examination, an optical examination mechanism is provided on a distal end of an insertion portion of the endoscope for endoscopic examination forwardly of the insertion portion. A probe insertion channel is disposed along the insertion portion so that a ultrasonic probe is passed therethrough. A probe guiding mechanism is disposed in the insertion portion to guide a distal end of the ultrasonic probe to project from the distal end of the insertion portion laterally of the distal end of the insertion portion.

5 Claims, 17 Drawing Sheets

ENDOSCOPE FOR ULTRASONIC EXAMINATION AND SURGICAL TREATMENT ASSOCIATED THERETO

BACKGROUND OF THE INVENTION

The present invention relates to an endoscope for ultrasonic examination and surgical treatment associated thereto.

In order to diagnose and treat a diseased part under the membrane in a body cavity, an ultrasonic probe capable of producing an ultrasonic cross-sectional image and a treatment tool such as an endoscopic injection tool have to be guided to an area near the diseased part via an endoscope.

To meet this need, one may think of using an endoscope for surgical treatment having two insertion channels. A two-channel endoscope is adapted to be such that the tips of both an ultrasonic probe and a treatment tool project in the direction in which examination is done with an optical viewing system.

In order to realize ultrasonic scan on the site being examined with the endoscope under a condition that the tip of the ultrasonic probe projects in the viewing field, the ultrasonic probe must be designed to transmit ultrasonic waves forward and receiving the reflected waves for scan.

On the other hand, the ultrasonic probe must be capable of passing through the channel in the endoscope, and therefore cannot be thicker than 2 to 3 mm. However, with such a small diameter, the probe for creating an ultrasonic cross-sectional image in a forward direction achieves only a very low resolution.

SUMMARY OF THE INVENTION

The present invention has been accomplished under these circumstances and has as an object providing an endoscope for ultrasonic examination, which is adapted for use with an ultrasonic probe capable of scanning by transmitting and receiving ultrasonic waves laterally of its tip and which can obtain a sharp ultrasonic cross-sectional image within a range of optical viewing area ahead of the foremost end of the insertion portion of the endoscope.

Another object of the present invention is to provide an endoscope for surgical treatment associated with the ultrasonic examination, which is adapted for use with an ultrasonic probe capable of scanning by transmitting and receiving ultrasonic waves laterally of its tip and which can obtain a sharp ultrasonic cross-sectional image of a diseased part under the membrane being optically examined while performing an endoscopic treatment on the diseased part.

To achieve the above-noted and other objects, the present invention provides an endoscope which comprises: an elongated insertion portion; a tip housing on a longitudinal end of the insertion portion; an optical imaging system provided in the tip housing and directed in a first direction; and a probe insertion channel extending along the insertion portion, and communicating with a probe projecting port disposed in the tip housing and opened in a second direction substantially lateral with respect to the first direction.

It is preferable that the endoscope further comprises a movable guide disposed within the probe projecting port.

It is preferable that the endoscope further comprises a treatment tool insertion channel extending along the insertion portion, and communicating with a treatment tool projecting port disposed in the tip housing and opened substantially in the first direction.

It is preferable that an endoscope further comprises a movable guide disposed within the treatment tool insertion channel.

It is preferable that the endoscope further comprises a second movable guide disposed within the probe projecting port.

It is preferable that the endoscope further comprises an ultrasonic probe removably passed through the probe insertion channel so that its tip end projects from the probe projecting port.

It is preferable that the endoscope further comprises: an adjusting mechanism which adjusts the direction in which the tip end of the ultrasonic probe projects from the probe projecting port.

It is preferable that the endoscope further comprises a wire extending along the insertion section and connected to the movable guide.

It is preferable that the endoscope further comprises a wire extending along the insertion section and connected to the movable guide.

The present invention provides an endoscope for ultrasonic examination, which comprises: an insertion portion; an optical examination mechanism provided on a distal end of the insertion portion for endoscopic examination forwardly of the insertion portion; a probe insertion channel disposed along the insertion portion so that a ultrasonic probe is passed therethrough; and a probe guiding mechanism disposed in the insertion portion to guide a distal end of the ultrasonic probe to project from the distal end of the insertion portion laterally of the distal end of the insertion portion.

It is preferable that the ultrasonic probe transmits and receives ultrasonic waves laterally of its distal end.

It is preferable that the probe guiding mechanism adjusts, through a remote operation, a projecting direction in which the distal end of the ultrasonic probe projects from the distal end of the insertion portion.

The present invention provides an endoscope for surgical treatment associated with ultrasonic examination, which comprises: an insertion portion; an optical examination mechanism provided on a distal end of the insertion portion for endoscopic examination forwardly of the insertion portion; a treatment tool insertion channel disposed along the insertion portion so that a treatment tool is passed therethrough; a probe insertion channel disposed along the insertion portion so that a ultrasonic probe is passed therethrough; a treatment tool projecting port by which a distal end of the treatment tool passed through the treatment tool insertion channel projects from the distal end of the insertion portion toward and within an examination viewing field of the optical examination mechanism; and a probe projecting port by which a distal end of the ultrasonic probe passed through the probe insertion channel projects from the distal end of the insertion portion in a direction away from an examination direction of the optical examination mechanism.

It is preferable that the ultrasonic probe transmits and receives ultrasonic waves laterally of its distal end.

It is preferable that the endoscope for surgical treatment associated with ultrasonic examination further comprises a probe projecting direction adjusting mechanism which adjusts, through a remote operation, a projecting direction in which the distal end of the ultrasonic probe projects from the distal end of the insertion portion.

It is preferable that the distal end of the ultrasonic probe projecting from the distal end of the insertion portion is located within a peripheral portion of the examination viewing field of the optical examination mechanism.

The present disclosure relates to the subject matter contained in Japanese patent application Nos. Hei. 10-178505 and Hei. 10-178506 (both filed on Jun. 25, 1998), which are expressly incorporated herein by reference in their entireties.

DESCRIPTION OF THE PREFERRED EMBODIMENT

An embodiment of the present invention is described below with reference to the accompanying drawings.

Figure 3:
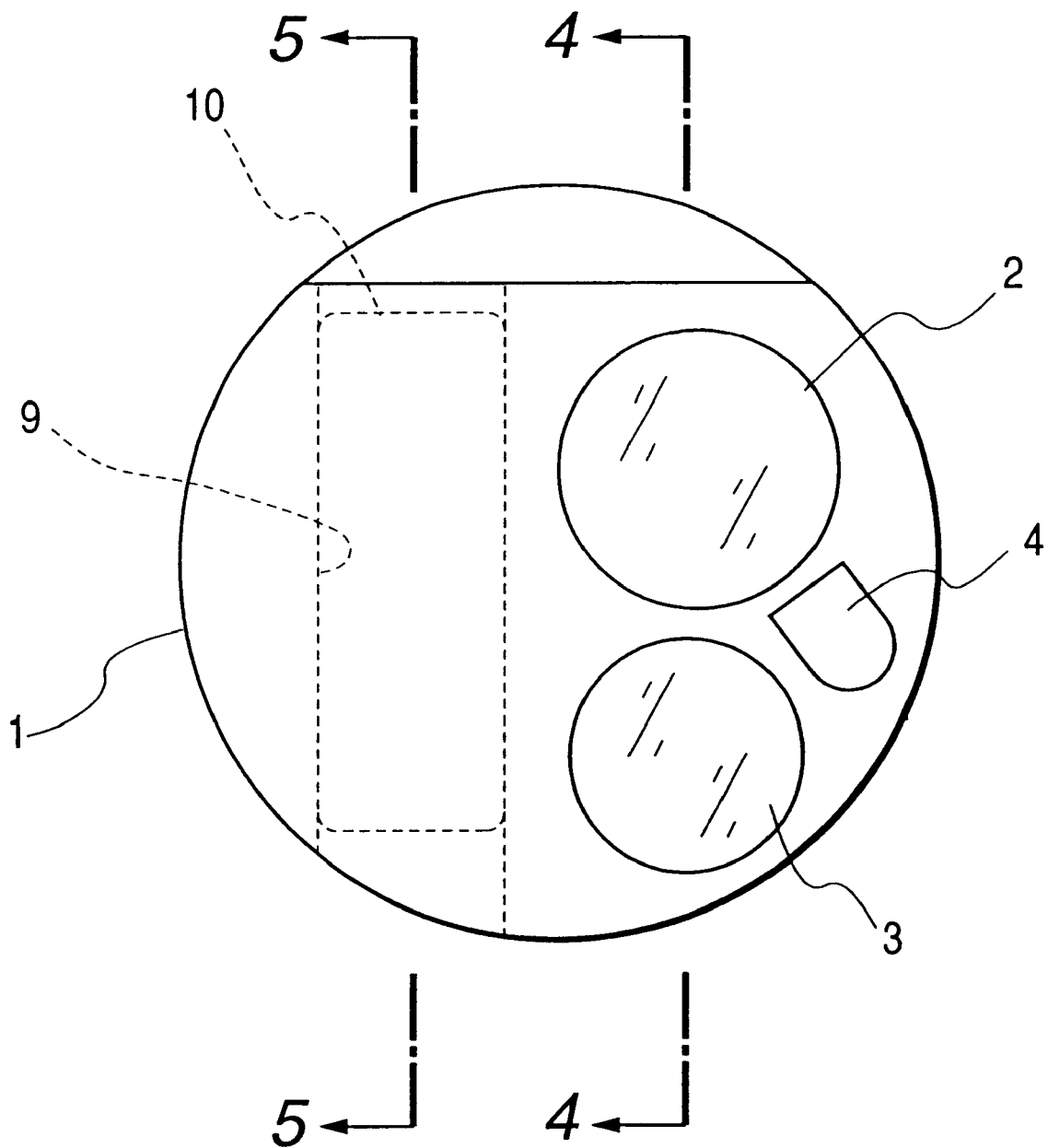
FIG. 3 is a front view of the same endoscope.

FIG. 3 shows the end face of the tip housing 1 forming the foremost end of the insertion portion of an endoscope and it has two juxtaposed windows, a viewing window 2 for optical examination and an illumination window 3 for illuminating the scope of optical examination. Shown by 4 is a nozzle for spraying the surface of the viewing window 2 with air and water.

Figure 4:
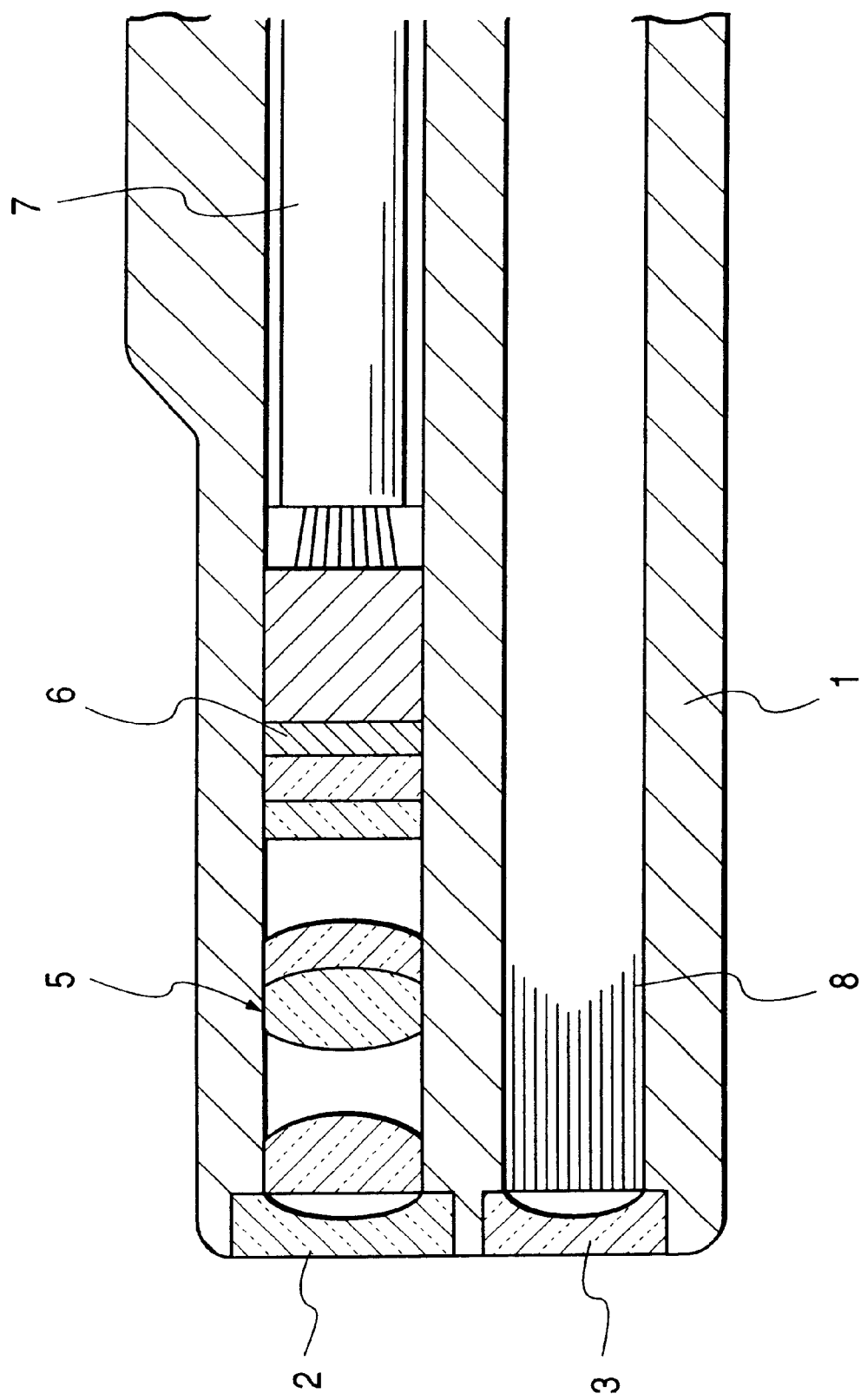
FIG. 4 is section 4—4 of FIG. 3.

FIG. 4 is section 4—4 of FIG. 3. As shown, objective optics 5 is provided rearward of the viewing window 2 to ensure that an object lying ahead of the housing tip 1 is focused at the imaging plane of a solid-state imaging device 6.

The focused optical image is sent over a signal cable 7 through the insertion portion to a video processor (not shown) so that an endoscopically examined image is displayed on a TV monitor. If desired, the combination of the solid-state imaging device 6 and the signal cable 7 may be replaced by an image guide fiber bundle.

The exit end of an illuminating lightguide fiber bundle 8 is provided rearward of the illumination window 3 and the illuminating light issued from the bundle 8 is projected to the object ahead of the tip housing 1.

Turning back to the FIG. 3, a probe projecting groove or probe projecting port 9 is formed in the tip housing 1 in a position juxtaposed to the viewing window 2 and the illumination window 3. A probe guide plate 10 is provided in the groove 9.

Figure 5:
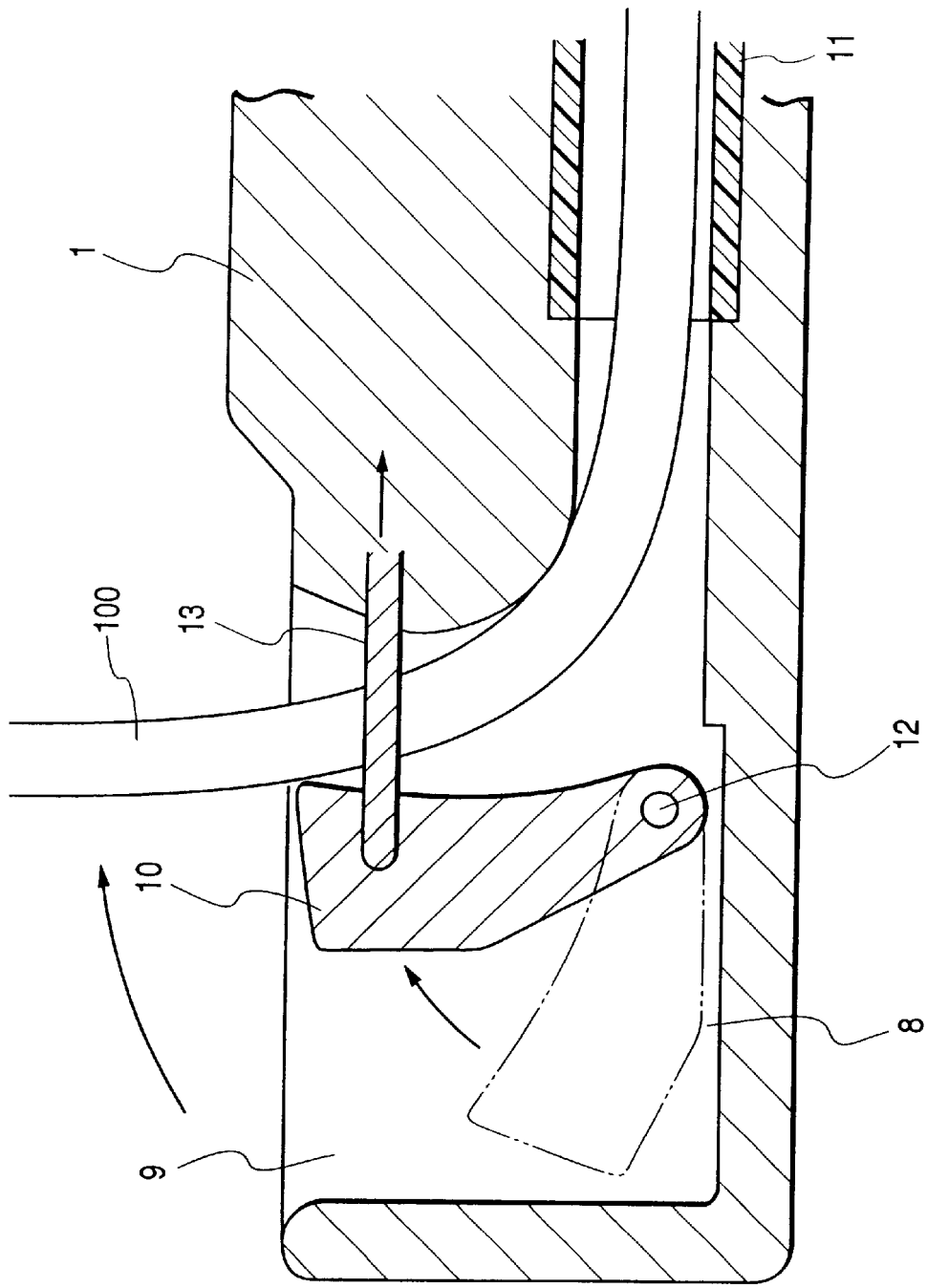
FIG. 5 is section 5—5 of FIG. 3.

FIG. 5 is section 5—5 of FIG. 3. As shown, the exit of a probe insertion channel 11 communicates with and connects to an area rearward of the probe projecting groove 9. The channel is typically formed of a PTFE (polytetrafluoroethylene) tube, and inserted into and arranged along the insertion portion of the endoscope. With this arrangement, the tip of an ultrasonic probe 100 inserted into the channel 11 is guided along the plate 10 so that it projects from the groove 9 to be directed laterally of the tip housing 1. It should be noted that the term "laterally" does not have the strict sense of being "perpendicular" to the longitudinal axis of the tip housing 1 but simply means "approximately lateral".

The probe guide plate 10 in the probe projecting groove 9 is pivotal about a shaft 12 supported on the tip housing 1. A handling section (not shown) is coupled to the end of the insertion portion which is the closer to the operator, and a maneuvering wire 13 that can be moved back and forth by remote operation of the handling section is coupled to the probe guide plate 10.

If the handling section is operated to move the maneuvering wire 13 back and forth, the probe guide plate 10 pivots within the probe projecting groove 9 such that the direction in which the tip of the ultrasonic probe 100 projects is adjustable over a broad range from a obliquely forward position with respect to the tip housing 1 to a lateral position substantially perpendicular to the longitudinal axis of the tip housing 1.

Figure 6:
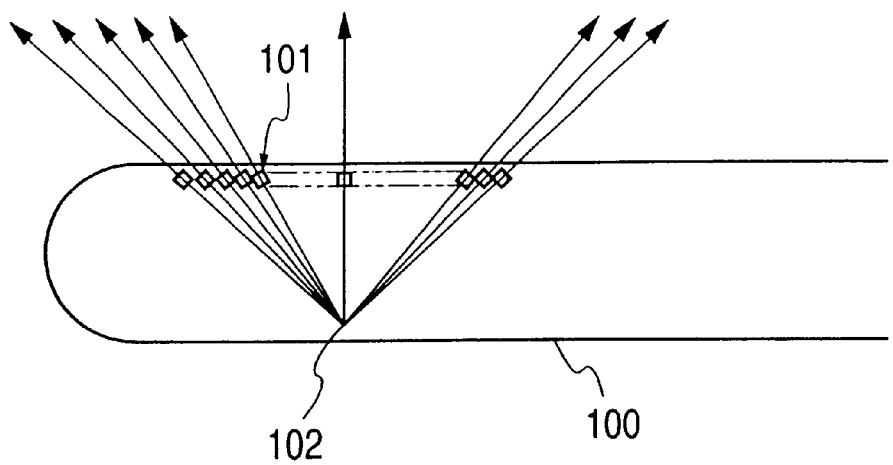
FIG. 6 is a simplified side view of the sector scanning ultrasonic probe shown in FIG. 1.
Figure 7:
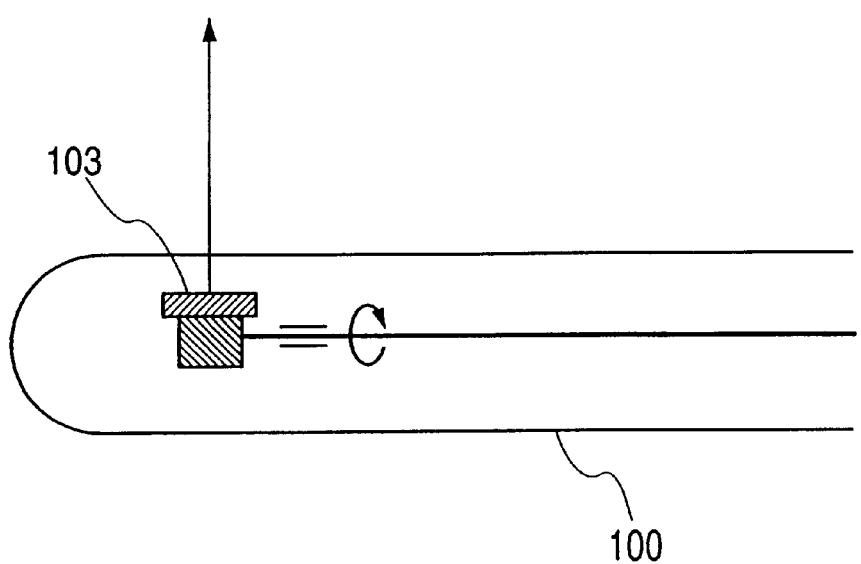
FIG. 7 is a simplified side view of the radial scanning ultrasonic probe shown in FIG. 2.

FIGS. 6 and 7 are illustrations of the ultrasonic probe 100 to be used with the endoscope for ultrasonic examination.

The ultrasonic probe 100 shown in FIG. 6 is of a so-called "sector scanning" type which has an ultrasonic oscillator array 101 provided on a lateral side near the tip; the array 101 is made up of a multiple of ultrasonic oscillators arranged parallel to its longitudinal axis.

As in a so-called "convex" type, ultrasonic waves are transmitted and received in a sector manner to scan a sectional range in both forward and backward directions in an area lateral to the longitudinal axis of the probe. To this end, the respective ultrasonic oscillators are arranged in directions perpendicular to single opposite point 102.

The ultrasonic probe 100 shown in FIG. 7 is of a so-called "radial scanning" type, in which a single ultrasonic oscillator 103 is driven to rotate about the longitudinal axis of the probe to scan in directions perpendicular to said axis through 360°.

Figure 1:
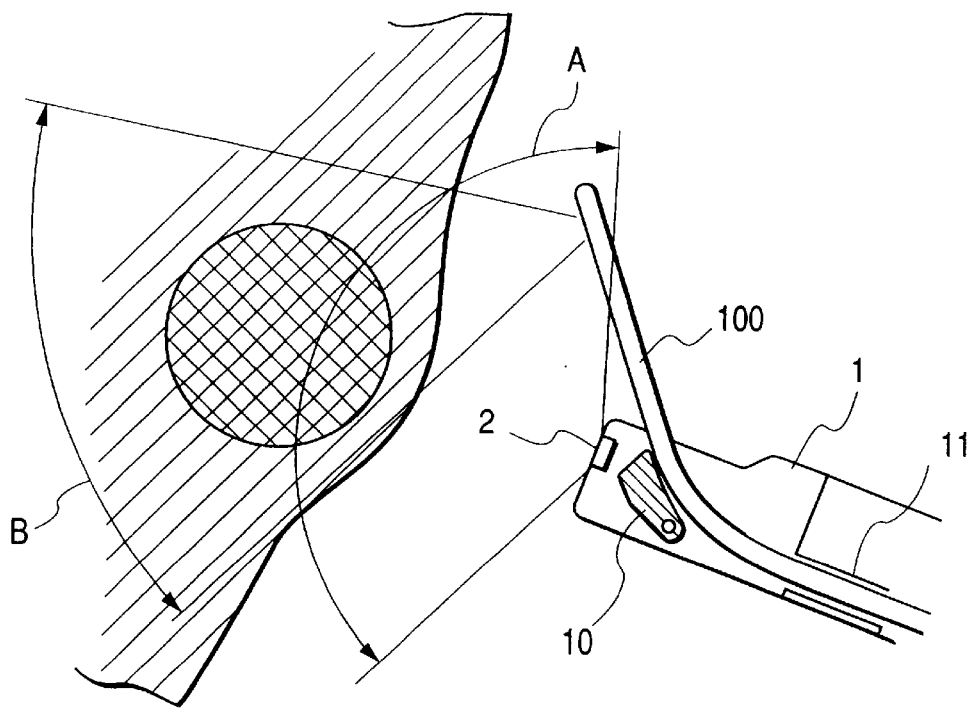
FIG. 1 is a sketch showing how a sector scanning ultrasonic probe is used with an endoscope for ultrasonic examination according to an embodiment of the invention.

FIG. 1 shows how the endoscope is used with the sector scanning ultrasonic probe 100 of FIG. 6 being inserted into the probe insertion channel 11. Since the tip of the probe 100 projects laterally of the tip housing 1, the ultrasonic scan range B substantially overlaps with the viewing field A ahead of the tip housing 1 so that a cross-section of a living tissue ahead of the viewing field A can be imaged by ultrasonic examination.

The ultrasonic scan range B can be adjusted by pivoting the probe guide plate 10 to change the direction in which the ultrasonic probe 100 projects. If the tip of the ultrasonic probe 100 is set such that its movement is at all times visible within the viewing field A (does not go beyond it), the operator can handle the endoscope with safety.

Figure 2:
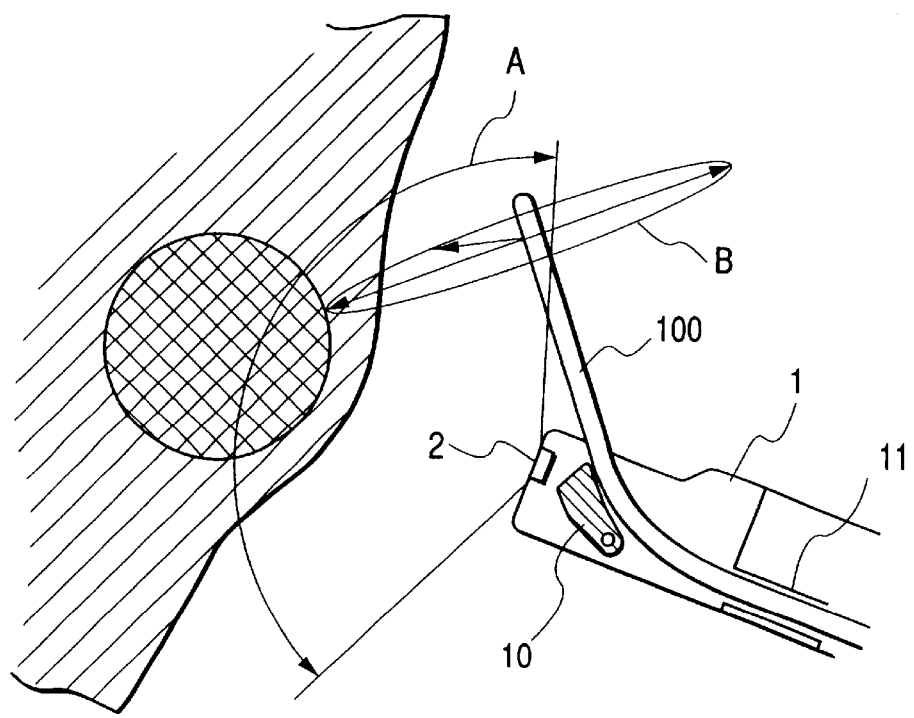
FIG. 2 is a sketch showing how a radial scanning ultrasonic probe is used with the same endoscope.

FIG. 2 shows how the endoscope is used with the radial scanning ultrasonic probe 100 of FIG. 2 being inserted into the prove insertion channel 11. Compared to the case shown in FIG. 1, a living tissue located ahead of the viewing field A which is forward of the tip housing 1 is scanned with ultrasonic waves through a section cut perpendicular to the longitudinal axis of the probe, thereby producing a cross-sectional image of the tissue.

Figure 9:
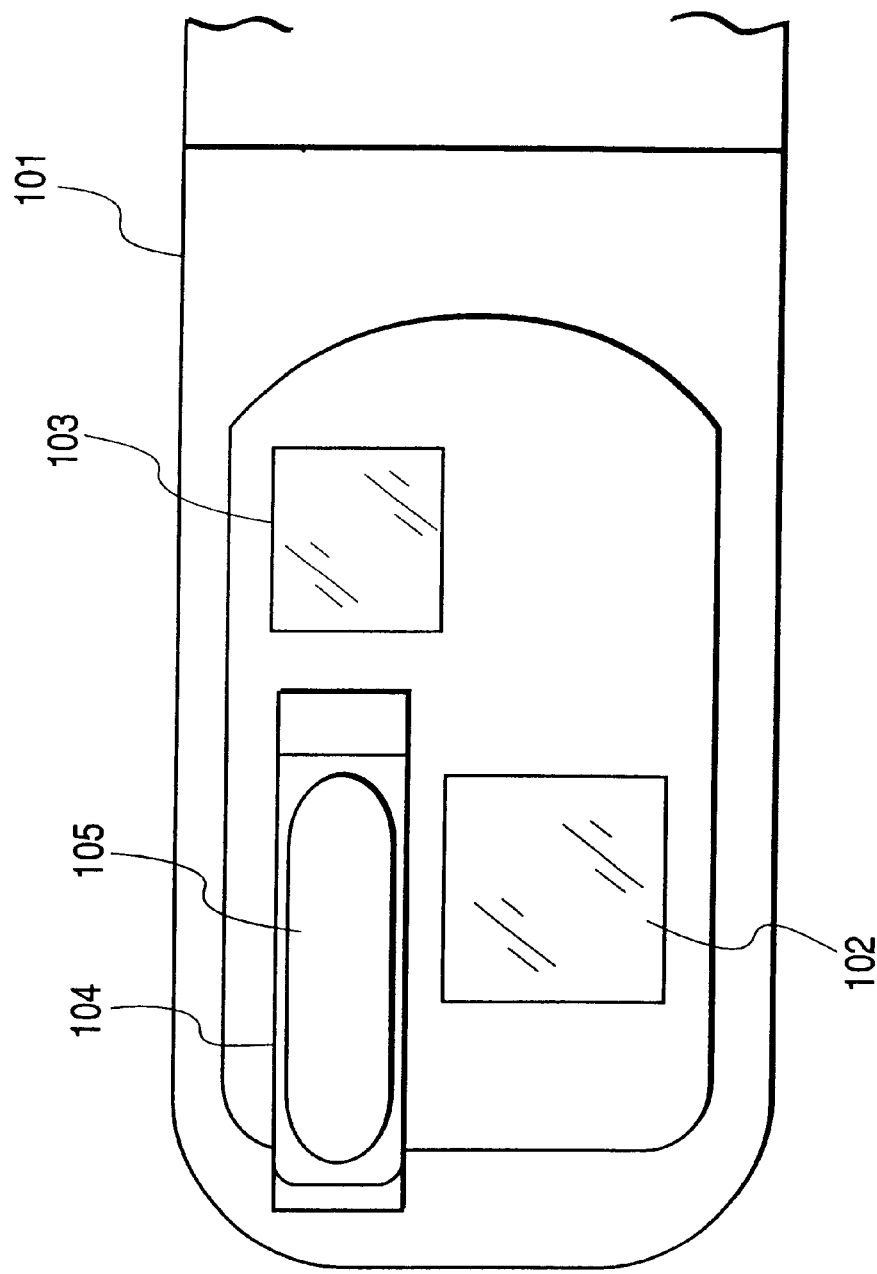
FIG. 9 is a plan view of the tip of the same endoscope.

FIG. 9 is a plan view of the tip of the insertion portion of a lateral viewing endoscope according to a second embodiment of the invention. As shown, a viewing window 102 for optical examination and an illumination window 103 for illuminating the scope of optical examination are provided on a lateral side of tip housing 101.

Shown by 104 is a treatment tool projecting port from which is projected the tip portion of a treatment tool inserted into a treatment tool insertion channel to be described below. The port 104 is formed as an elongated groove extending in a direction parallel to the longitudinal axis of the tip housing 101. It is open to the same lateral side of the tip housing 101 where the viewing window 102 is made; thus, the treatment tool projecting port 104 and the viewing window 102 lie side by side. A treatment tool erecting plate 105 for adjusting the direction in which the treatment tool projects is provided within the port 104.

Figure 8:
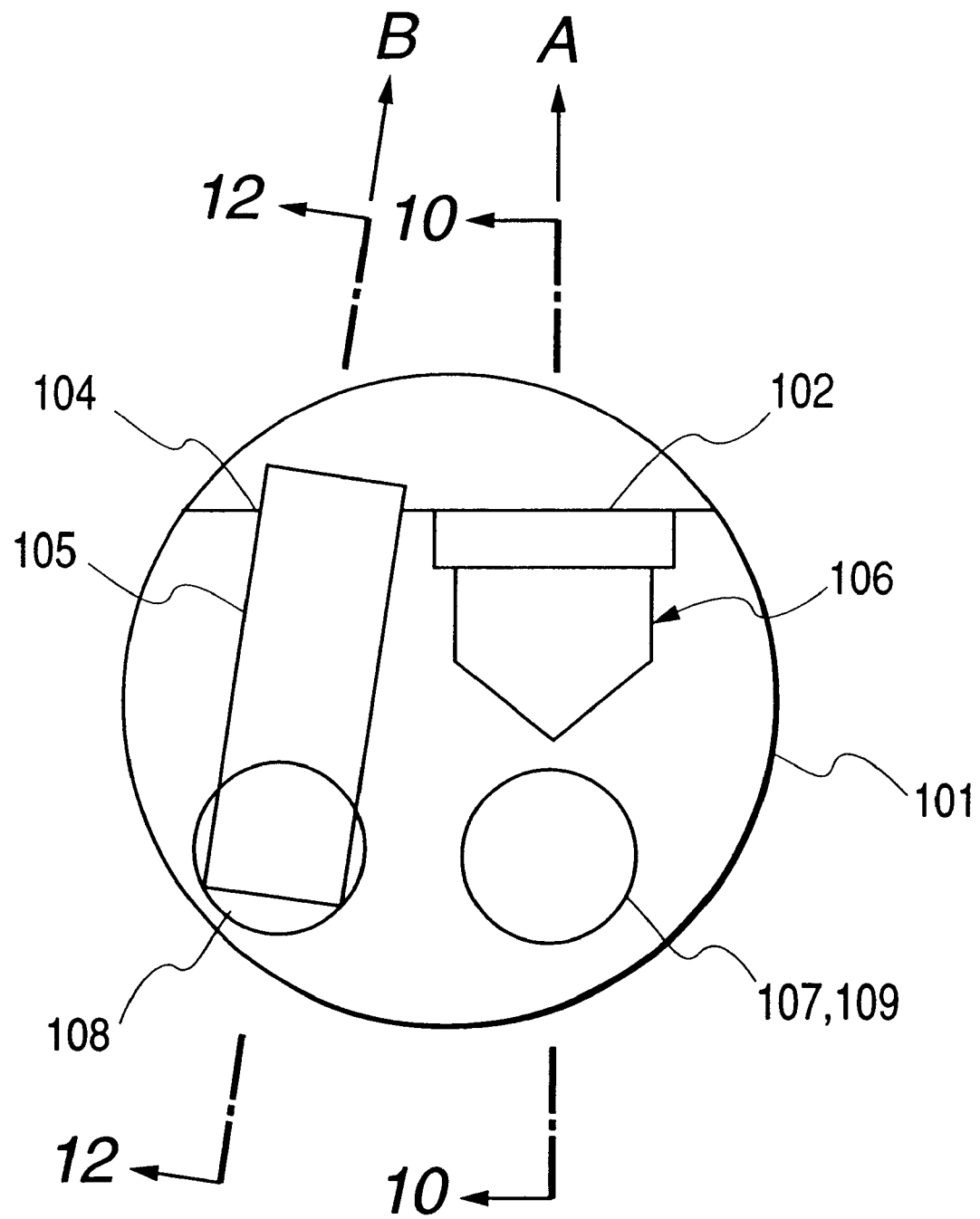
FIG. 8 is a perspective view of the tip of a forward viewing endoscope, as seen from the front, according to another embodiment of the invention.

FIG. 8 is a perspective view of the tip of the insertion portion as seen from the front. Objective optics 106 is provided rearward of the viewing window 102 and further rearward is provided a probe insertion channel 107 through which an ultrasonic probe is to be inserted. The treatment tool projecting port 104 communicates with and connects to a treatment tool insertion channel 108 through which a treatment tool is to be inserted.

Figure 10:
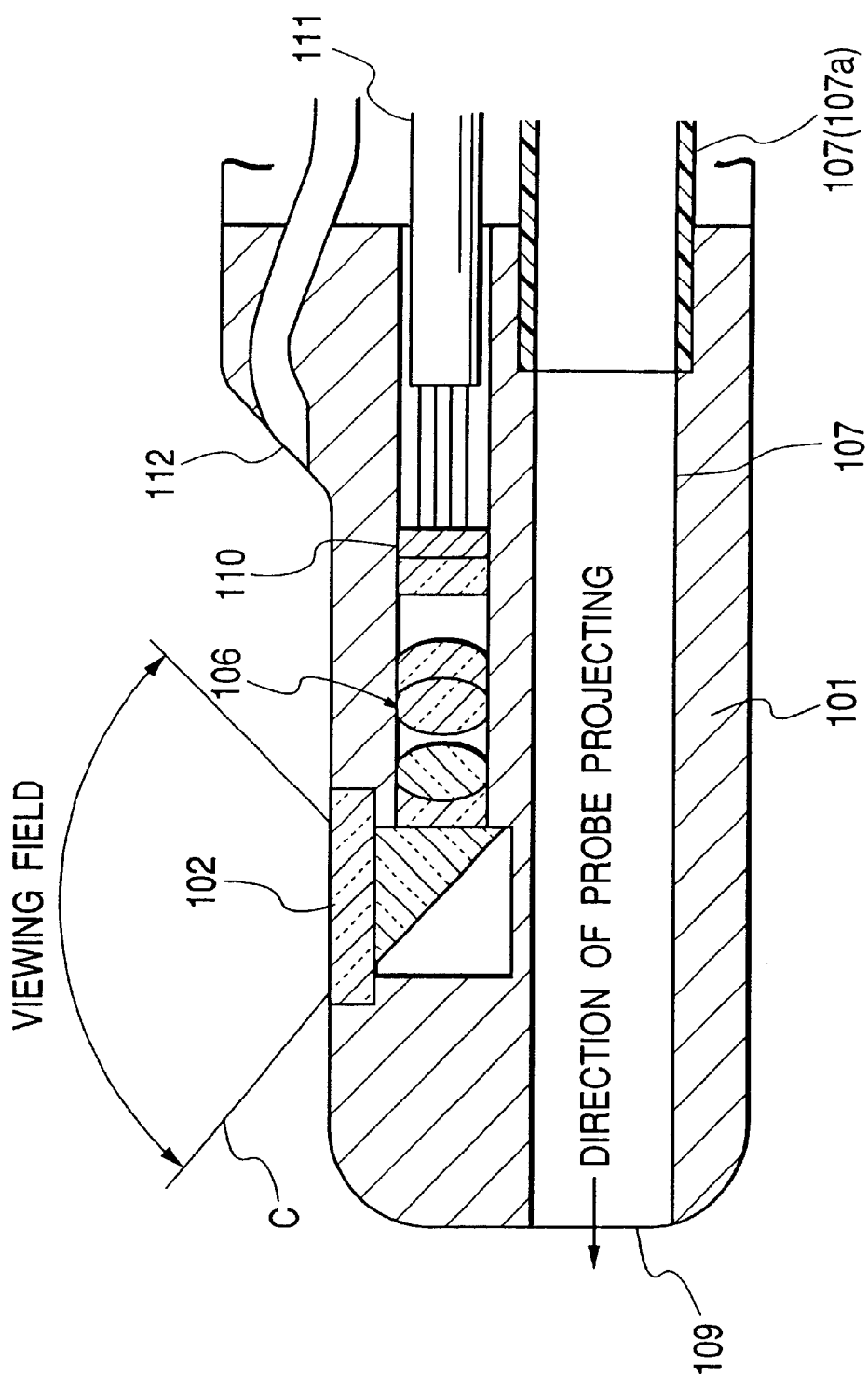
FIG. 10 is side section 10—10 of FIG. 8.

FIG. 10 is section 10—10 of FIG. 8. As shown, the objective optics 106 provided rearward of the viewing window 102 ensures that an object lying lateral to the tip housing 101 is focused at the imaging plane of a solid-state imaging device 110. Shown by 112 is a nozzle for spraying the surface of the viewing window 102 with air and water.

The focused optical image is sent over a signal cable 111 through the insertion portion to a video processor (not shown) so that an endoscopically examined image is displayed on a TV monitor. If desired, the combination of the solid-state imaging device 110 and the signal cable 111 may be replaced by an image guide fiber bundle.

The probe insertion channel 107 is coupled to the tip housing 101; it is a flexible tube 107a that is typically formed of PTFE (polytetrafluoroethylene) and which is passed through substantially the entire length of the insertion portion. An ultrasonic probe projecting port 109 is open in the front end face of the tip housing 101 to be directed forward of the insertion portion.

With this arrangement, the tip of the ultrasonic probe inserted into the channel 107 projects from the port 109 in a direction perpendicular to the optical axis of illuminating light so that it does not interfere with the viewing field.

Figure 11:
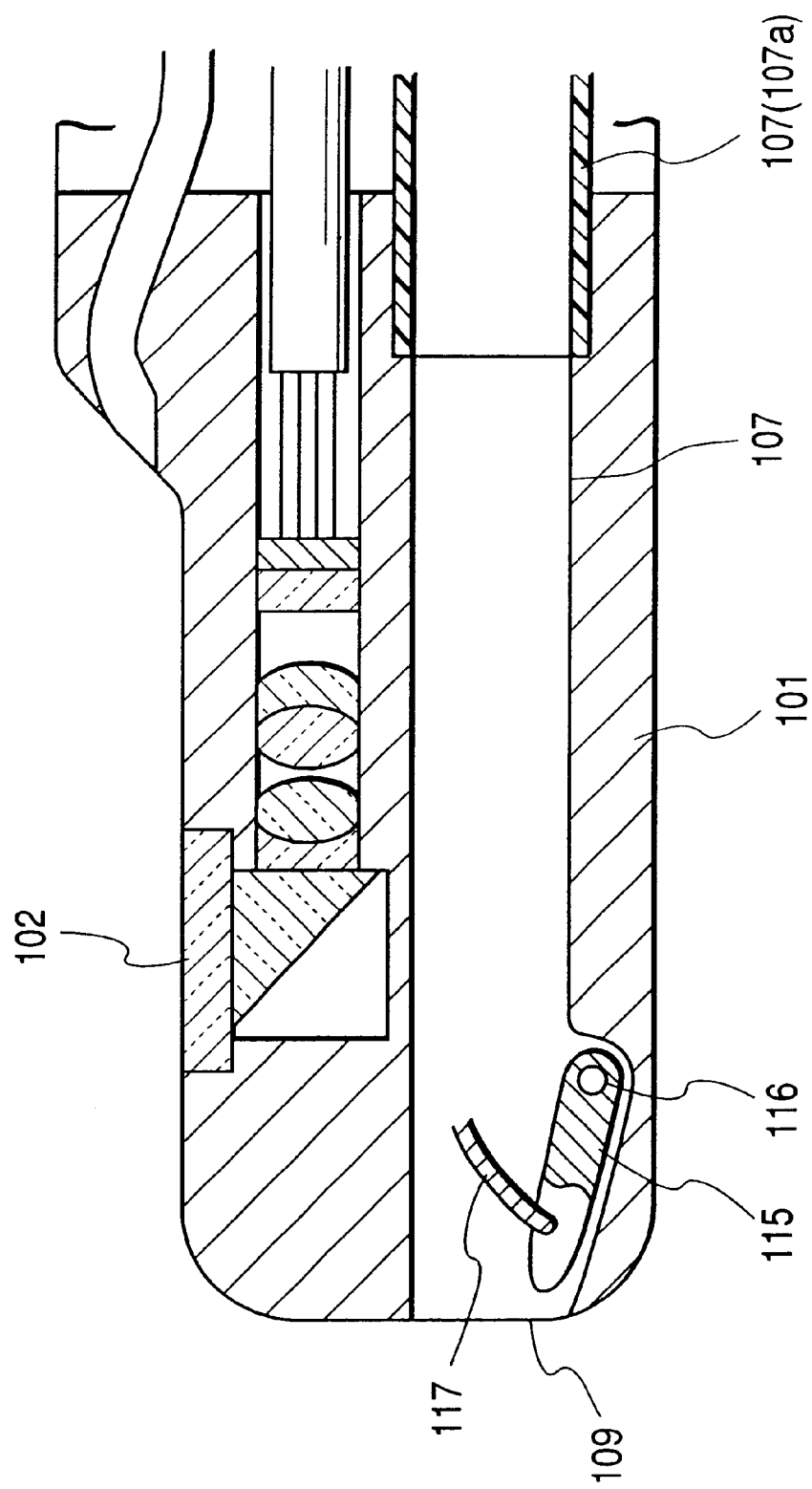
FIG. 11 is another example of side section 10—10 of FIG. 8.

As shown in FIG. 11, a probe erecting plate 115 for adjusting the direction in which the tip portion of the ultrasonic probe projects may be provided within the ultrasonic probe projecting port 109 as similarly to the first embodiment.

Further referring to FIG. 11, the probe erecting plate 115 is pivotal about a shaft 116 supported on the tip housing 101. A handling section (not shown) is coupled to the end of the insertion portion which is the closer to the operator and a maneuvering wire 117 that can be moved back and forth by remote operation of the handling section is coupled to the probe erecting plate 115.

If the handling section is operated to move the maneuvering wire 117 back and forth, the probe erecting plate 115 pivots such that the direction in which the tip of the ultrasonic probe projects from the port 109 is adjustable to any angle.

Figure 12:
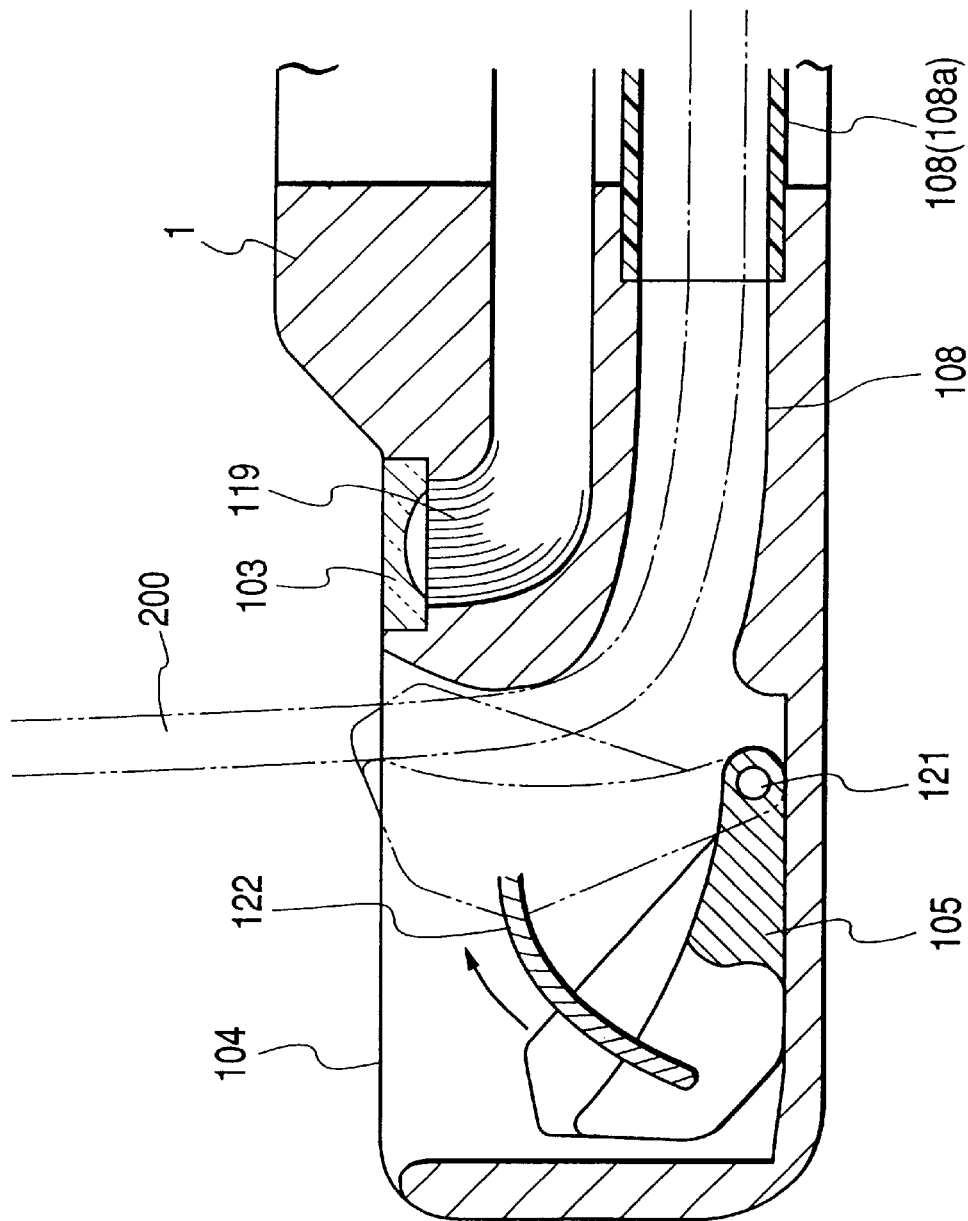
FIG. 12 is side section 12—12 of FIG. 8.

FIG. 12 is section 12—12 of FIG. 8. As shown, the exit end of an illuminating lightguide fiber bundle 119 is provided rearward of the illumination window 103 and the illuminating light issued from the bundle 119 is projected to the object lying lateral to the tip housing 101.

The treatment tool insertion channel 108 is coupled to the tip housing 101; it is a flexible tube 108a that is typically formed of PTFE (polytetrafluoroethylene) and which is passed through substantially the entire length of the insertion portion. A treatment tool inserted into the channel 108 can have its tip guided along the treatment tool erecting plate 105 to project from the port 104 laterally of the tip housing 101.

The treatment tool erecting plate 105 is pivotal about a shaft 121 supported on the tip housing 101. A maneuvering wire 122 coupled to the plate 105 can be moved back and forth by remote operation of the handling section coupled to the end of the insertion portion which is the closer to the operator.

If the handling section is operated to move the maneuvering wire 122 back and forth, the treatment tool erecting plate 5 pivots within the port 104 such that the direction in which the tip of the treatment tool projects is adjustable over a broad range from a obliquely forward position with respect to the tip housing 101 to a lateral position substantially perpendicular to the longitudinal axis of the tip housing 101.

Note that the treatment tool projecting port 104 is inclined to the optical axis A of the viewing light so that the direction B in which the treatment tool projects is toward the center of the viewing field (see FIG. 8).

Figure 13:
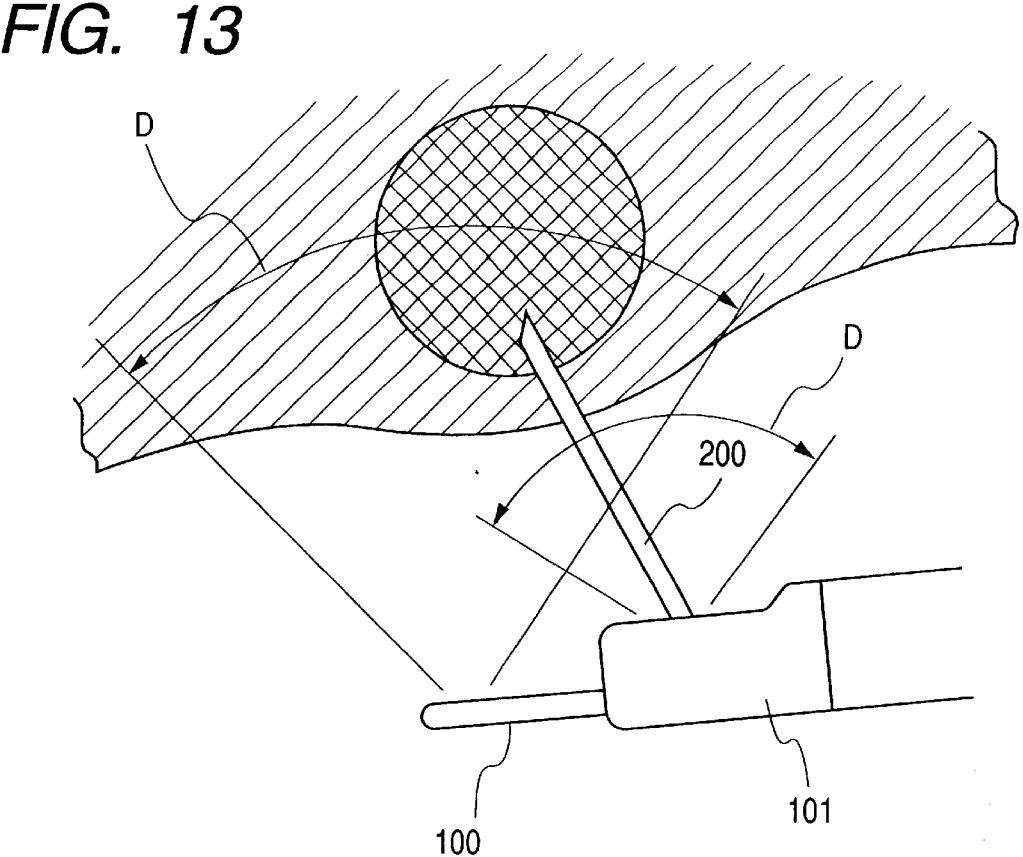
FIG. 13 is a sketch showing how the forward viewing endoscope according to the second embodiment of the invention is used in practice.

FIG. 13 shows how the endoscope according to the second embodiment is used with the sector scanning ultrasonic probe 100 of FIG. 6 being inserted into the probe insertion channel 107 and an endoscopic injection tool 200 into the treatment tool insertion channel 108. Since the tip of the ultrasonic probe 100 projects forward of the tip housing 101, the ultrasonic scan range D substantially overlaps with the viewing field C lateral to the tip housing 1 so that an ultrasonic cross-sectional image ahead of the viewing field C can be taken.

On the other hand, the tip of the injection tool 200 projects laterally from the tip housing 101, so it can be pierced toward the diseased part under the membrane within the viewing field C and the ultrasonic scan range D and at a sufficiently large angle (close to 90°) with respect to the membrane surface to enable the necessary treatment to be performed.

Figure 14:
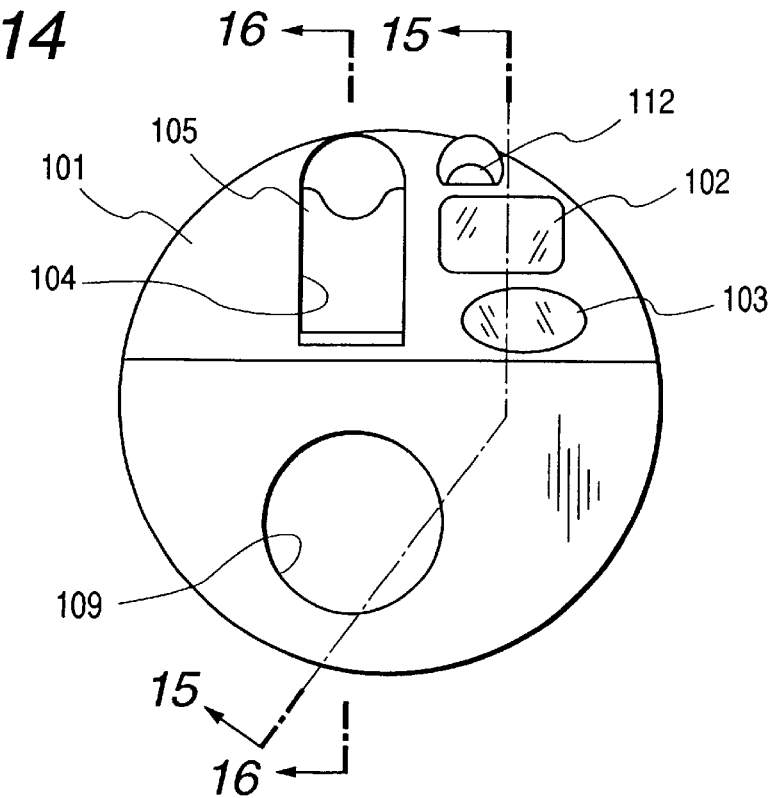
FIG. 14 is a front view of the tip of an oblique viewing endoscope according to a third embodiment of the invention.

FIG. 14 shows a third embodiment of the invention by a front view of the tip of the insertion portion of an oblique viewing endoscope to which the concept of the invention is applied. The components having the same functions as in the second embodiment are identified by like numerals and will not be described in detail.

Figure 15:
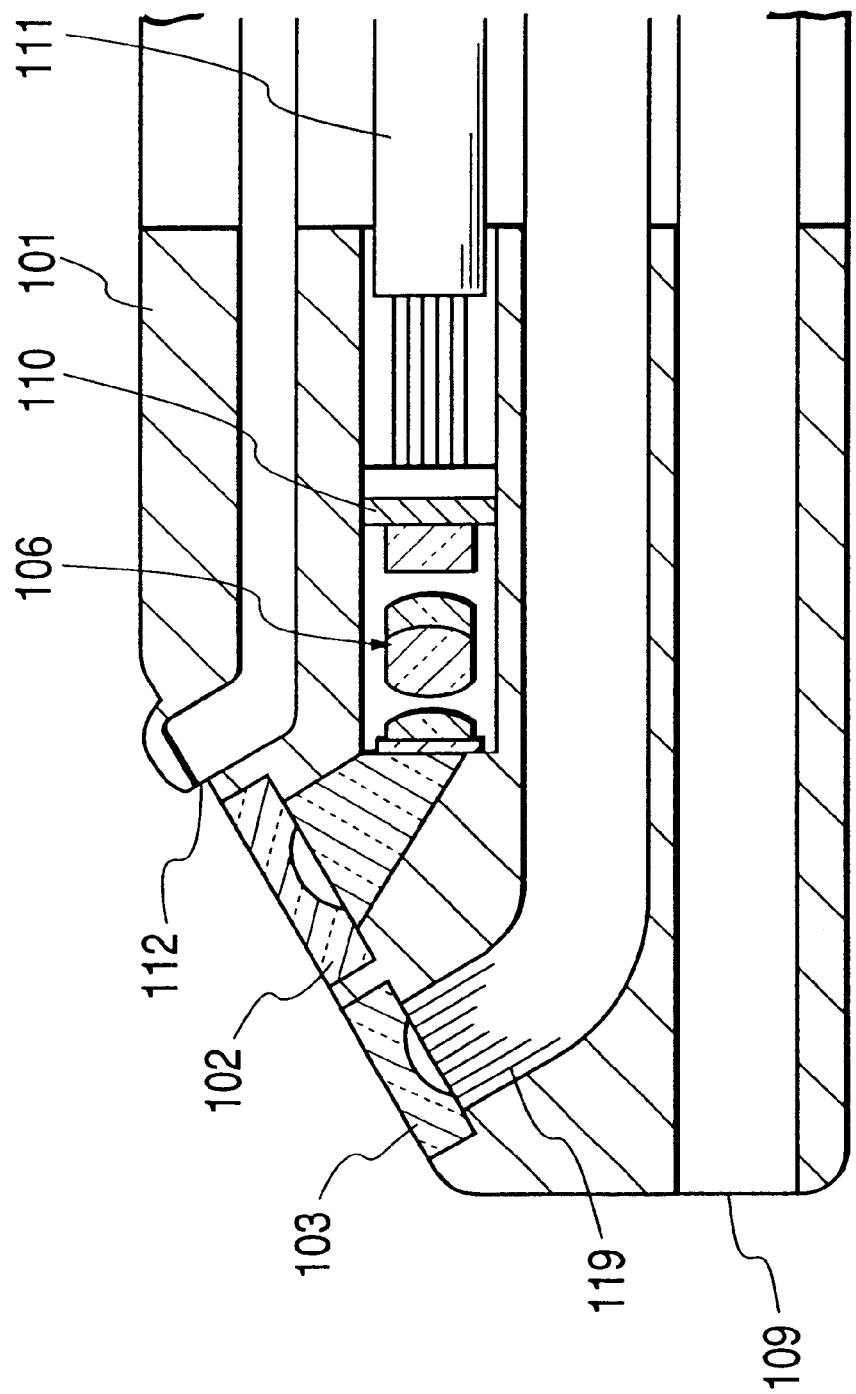
FIG. 15 is side section 15—15 of FIG. 14.

FIG. 15 is section 15—15 of FIG. 14. As shown, the upper half of the end face of the tip housing 101 is cut obliquely and the viewing window 102 and the illumination window 103 are arranged side by side on the oblique face so that an object situated obliquely forward of the tip housing 1 can be examined optically.

Figure 16:
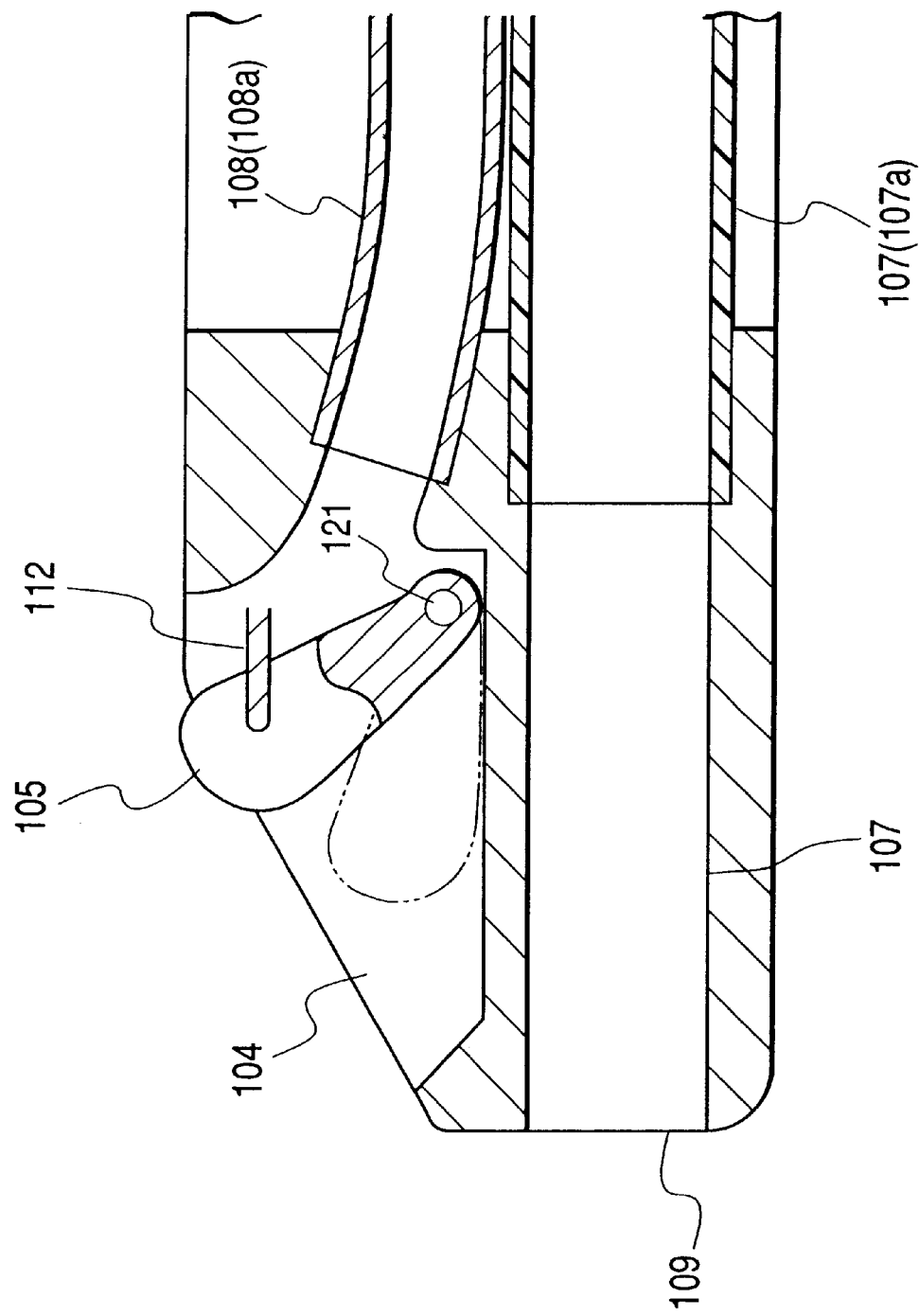
FIG. 16 is side section 16—16 of FIG. 14.

FIG. 16 is section 16—16 of FIG. 14. As in the second embodiment, the ultrasonic probe projecting port 109 is formed as an opening in the end face of the tip housing 101 so that the tip of the ultrasonic probe projects forward (parallel to the longitudinal axis of the tip housing 101).

The treatment tool projecting port 104 is formed as an opening in the oblique face of the tip housing 101 so that the tip of a treatment tool inserted into the treatment tool insertion channel 108 projects in a direction toward the viewing field obliquely ahead of the tip portion 101. The direction of its projection can be adjusted by the mechanism of the treatment tool erecting plate 105 positioned within the treatment tool projecting port 104.

Figure 17:
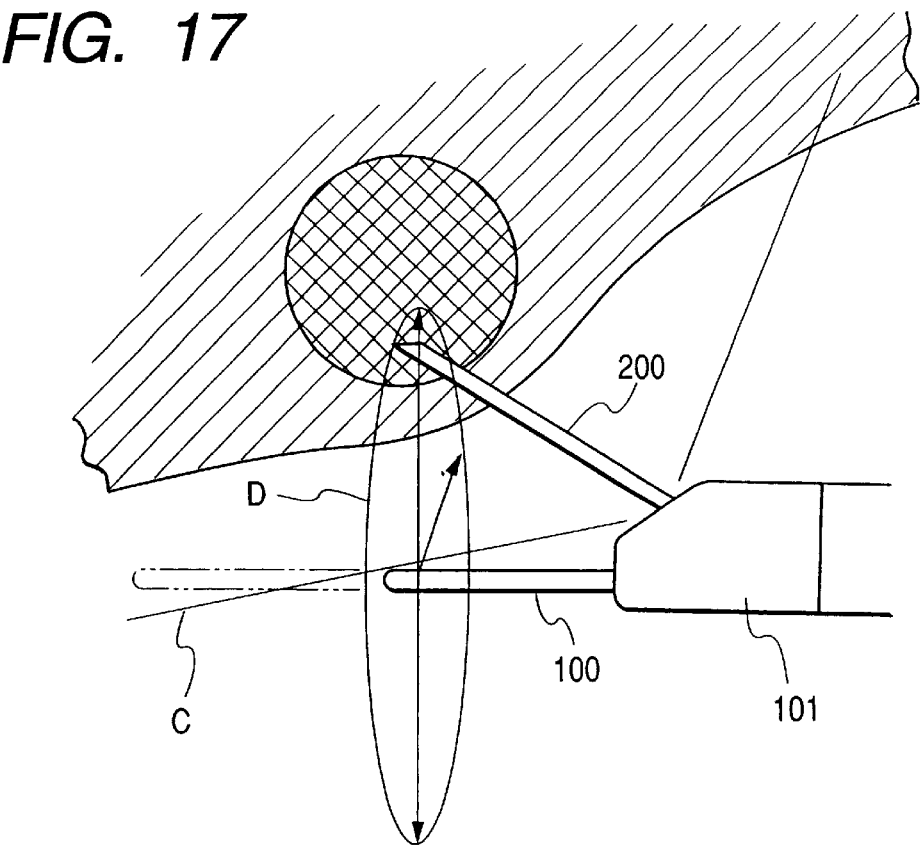
FIG. 17 is a sketch showing how the oblique viewing endoscope according to the third embodiment of the invention is used in practice.

FIG. 17 shows how the oblique viewing endoscope according to the third embodiment is used with the radial scanning ultrasonic probe 100 of FIG. 7 being inserted into the probe insertion channel 107 and an endoscopic injection tool 200 into the treatment tool insertion channel 108.

Again, the tip of the ultrasonic probe 100 projects ahead of the tip housing 101, so a desired ultrasonic cross-sectional image can be obtained by scanning through the viewing field C lying obliquely ahead of the tip portion 101.

Subsequently, the tip of the injection tool 200 is allowed to project from the tip housing 101 to an obliquely forward position until it is pierced into the diseased part under the membrane within the viewing field C and the ultrasonic scan range D to enable the necessary treatment to be performed. If the tip of the ultrasonic probe 100 is set such that its movement is at all times visible within the viewing field C (does not go beyond it), the operator can handle the endoscope with safety.

Figure 18:
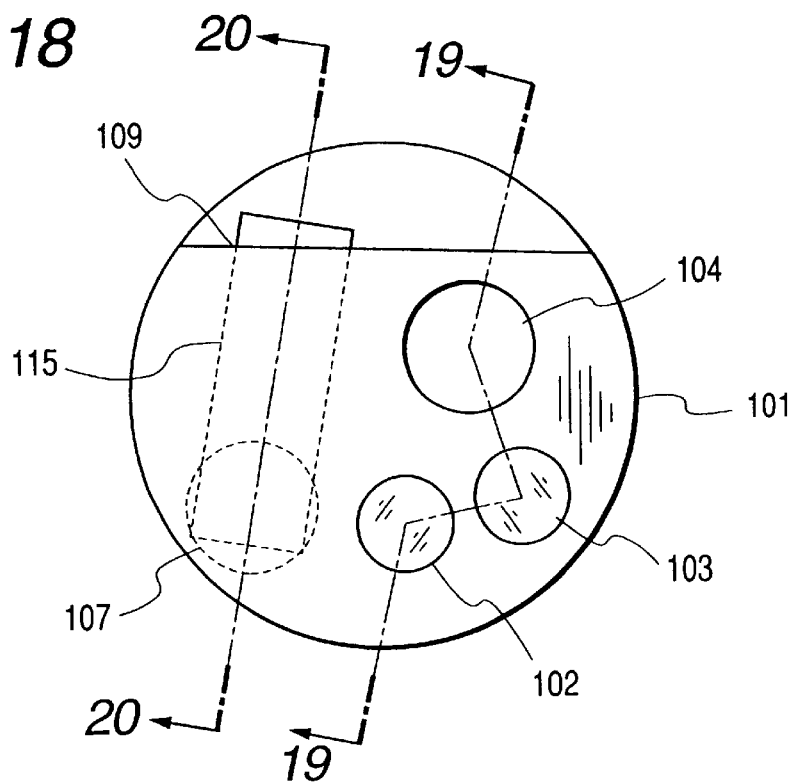
FIG. 18 is a front view of the tip of a lateral viewing endoscope according to a fourth embodiment of the invention.

FIG. 18 shows a fourth embodiment of the invention by a front view of the tip of the insertion portion of a forward viewing endoscope to which the concept of the invention is applied. The components having the same functions as in the second and third embodiments are identified by like numerals and will not be described in detail.

Figure 19:
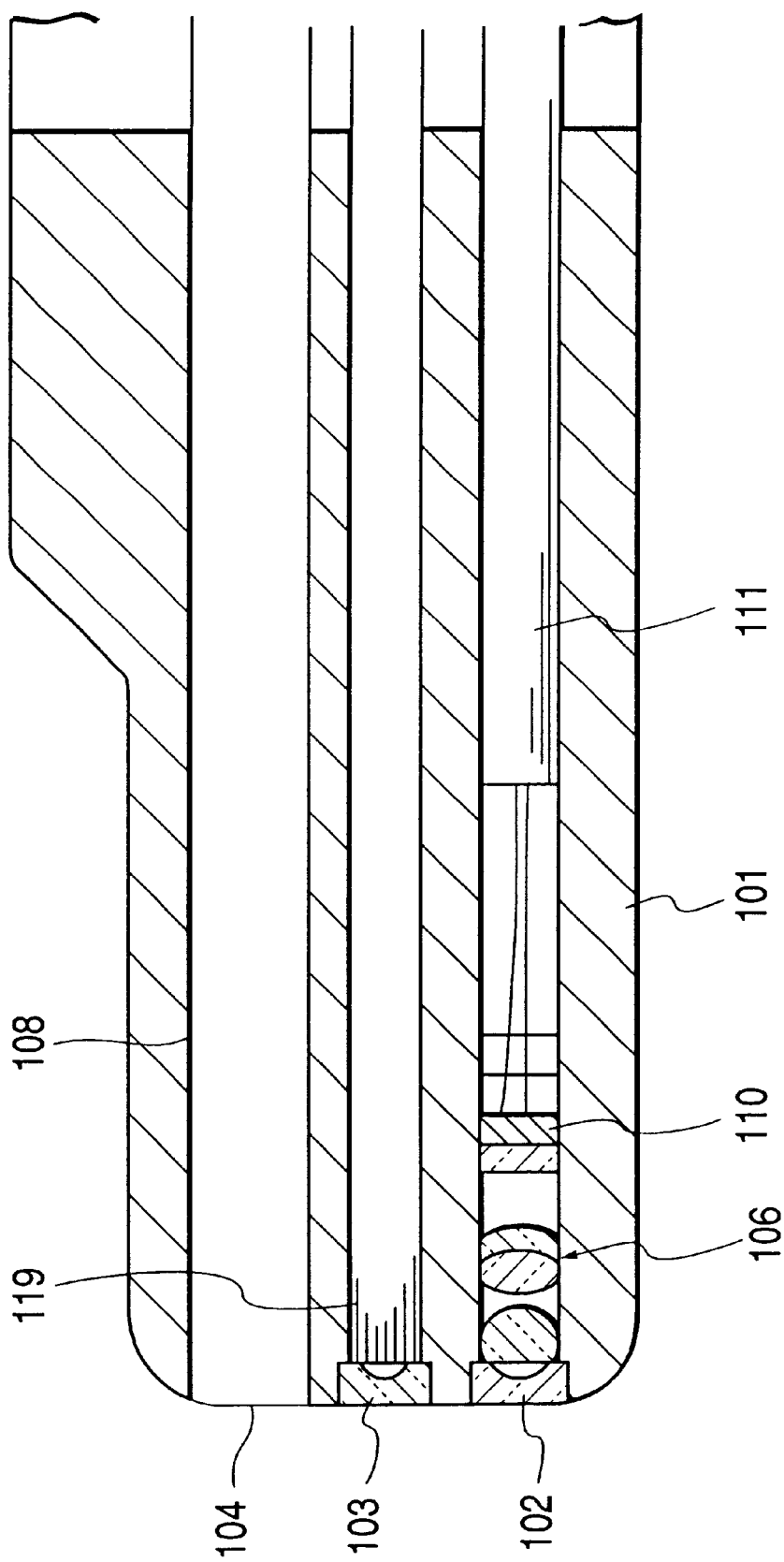
FIG. 19 is side section 19—19 of FIG. 18.

As also shown in FIG. 19 which is section 19—19 of FIG. 18, the viewing window 2 and the illumination window 3 are arranged side by side on the end face of the tip housing 101 in the fourth embodiment and this allows for optical viewing of an object lying ahead of the tip housing 101.

The treatment tool insertion channel 108 formed parallel to the longitudinal axis of the tip housing 101 extends straight to make an opening (treatment tool projecting port 104) in the end face of the tip housing 101, through which the tip of the treatment tool inserted into the channel 108 projects in a forward viewing direction.

Figure 20:
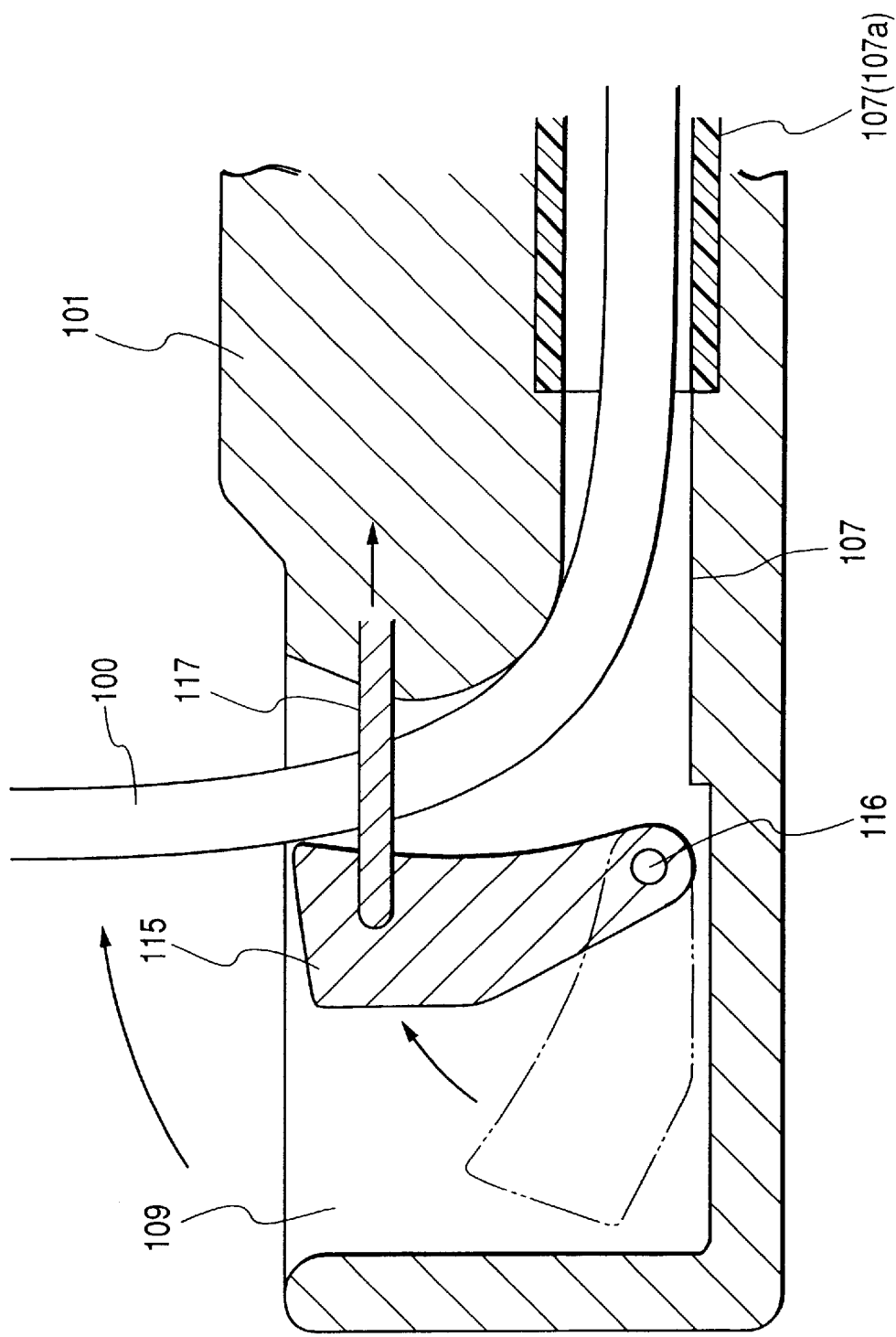
FIG. 20 is side section 20—20 of FIG. 18.

As shown in FIG. 20 which is section 20—20 of FIG. 18, the ultrasonic probe projecting port 109 is formed as an opening in a lateral side of the tip housing 1 so that the tip of the ultrasonic probe 100 inserted into the probe insertion channel 107 can be projected in a direction lateral to the tip housing 101.

The direction in which the ultrasonic probe 100 projects can be adjusted to any angle by remote operation of the probe erecting plate 115 provided within the probe projecting port 109. Shown by 116 is a shaft supported on the tip housing 101, and 117 is a maneuvering wire that is moved back and forth by operation of the handling section.

Figure 21:
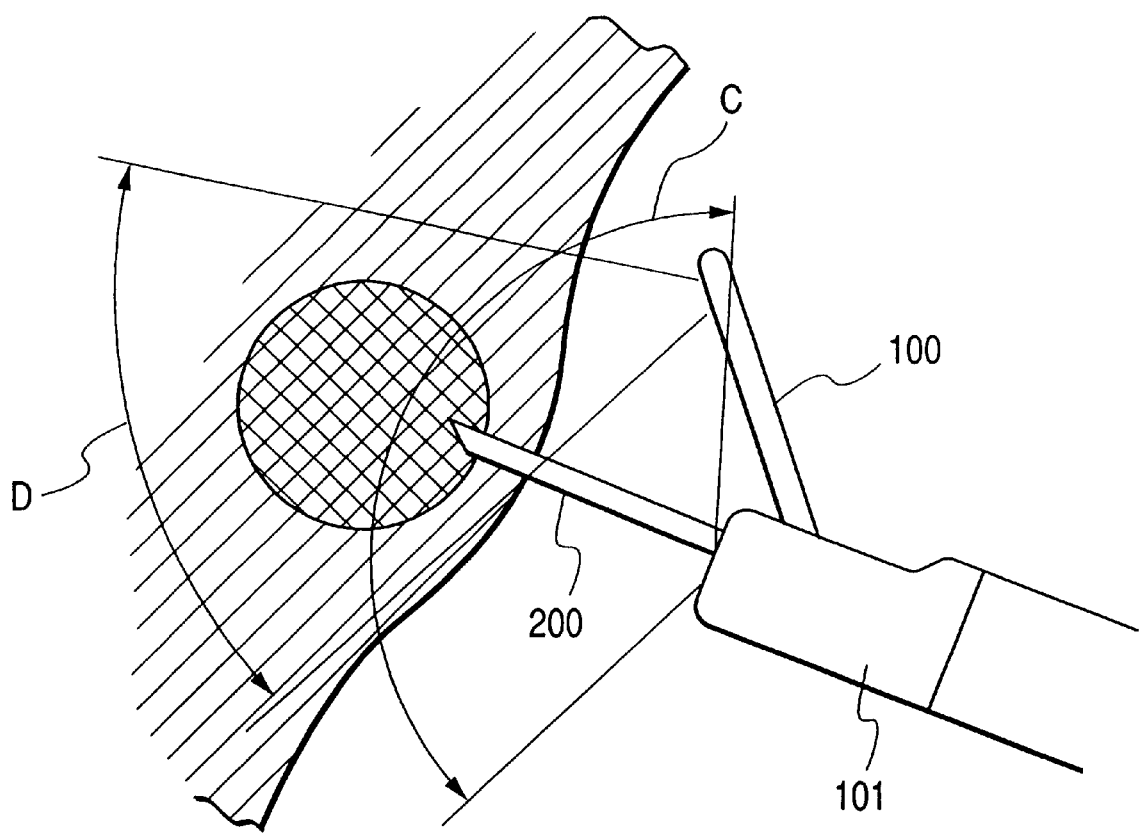
FIG. 21 is a sketch showing how the lateral viewing endoscope according to the fourth embodiment of the invention is used in practice.

FIG. 21 shows how the forward viewing endoscope according to the fourth embodiment of the invention is used with the sector scanning ultrasonic probe 100 of FIG. 6 being inserted into the probe insertion channel 107 and an endoscopic injection tool 200 into the treatment tool insertion channel 108.

In the case under consideration, the tip of the ultrasonic probe 100 projects laterally of the tip housing 101 so that the viewing field C lying ahead of the tip portion 101 can be scanned to produce an ultrasonic cross-sectional image.

Subsequently, the tip of the injection tool 200 is allowed to project forward from the tip housing 101 until it is pierced into the diseased part under the membrane within the viewing field C and the ultrasonic scan range D to enable the necessary treatment to be performed. As in the case shown in FIG. 17, if the tip of the ultrasonic probe 100 is set such that its movement is at all times visible within the viewing field C (does not go beyond it), the operator can handle the endoscope with safety.

What is claimed is:

1. An endoscope for surgical treatment associated with ultrasonic examination, comprising:

an insertion portion;

an optical examination mechanism with a viewing field facing in a first direction relative to the distal end of the insertion portion;

a treatment tool insertion channel disposed along the insertion portion so that a treatment tool is passable therethrough;

a probe insertion channel disposed along the insertion portion so that an ultrasonic probe is passable therethrough;

a treatment tool projecting port by which a distal end of the treatment tool passing through the treatment tool insertion channel projects from the distal end of the insertion portion; and a probe projecting port by which a distal end of the ultrasonic probe passing through the probe insertion channel projects from the distal end of the insertion portion in a direction different than the first direction, the distal end of the ultrasonic probe having an ultrasonic scan range substantially lateral to said insertion portion and at least partly overlapping the examination viewing field;

wherein a distal end of said treatment tool extends into the overlapping portion of the viewing field and the ultrasonic scan range.

2. An endoscope for surgical treatment associated with ultrasonic examination according to claim 1, wherein the ultrasonic probe transmits and receives ultrasonic waves laterally of its distal end.

3. An endoscope for surgical treatment associated with ultrasonic examination according to claim 1, further comprising:

a probe projecting direction adjusting mechanism which adjusts, through a remote operation, a projecting direction in which the distal end of the ultrasonic probe projects from the distal end of the insertion portion.

4. An endoscope for surgical treatment associated with ultrasonic examination according to claim 1, wherein the distal end of the ultrasonic probe projecting from the distal end of the insertion portion is located within a peripheral portion of the examination viewing field of the optical examination mechanism.

5. The endoscope for ultrasonic examination of claim 1, an oblique face provided on a distal end of said insertion portion, said treatment tool projecting from the oblique face and into the viewing field of said optical examination mechanism.

\* \* \* \* \*